United States Patent [19]

Takeuchi et al.

[11] Patent Number: 5,003,055

[45] Date of Patent: Mar. 26, 1991

[54] ANTHRACYCLINE DERIVATIVES HAVING INHIBITORY ACTIVITY AGAINST REVERSE TRANSCRIPTASE OF HUMAN IMMUNODEFICIENCY VIRUS

[75] Inventors: Tomio Takeuchi, Tokyo; Shinichi Kondo, Yokohama; Daishiro Ikeda; Yoshiyuki Koyama, both of Tokyo; Keiichi Ajito, Yokohama; Kazuo Umezawa; Sonoko Hirose, both of Tokyo, all of Japan

[73] Assignee: Zaidan Hojin Biseibutsu Kagaku Kenkyu Kai, Tokyo, Japan

[21] Appl. No.: 248,417

[22] Filed: Sep. 23, 1988

[30] Foreign Application Priority Data

Sep. 25, 1987 [JP] Japan .............................. 62-238972
Feb. 23, 1988 [JP] Japan .............................. 63-38567

[51] Int. Cl.$^5$ ........................................... C07H 15/24
[52] U.S. Cl. ................................................. 536/6.4
[58] Field of Search ........................... 536/6.4; 514/34

[56] References Cited

FOREIGN PATENT DOCUMENTS 0083228 1/1983 European Pat. Off. .
2272647 9/1975 France .
2025410 10/1980 United Kingdom .

OTHER PUBLICATIONS

Arcamone et al., "Synthesis and Biological Evaluation of Some 14–O–Aryl Derv. of Adriamycin", *J. of Medicinal Chemistry*, (1974) vol. 17(3) pp. 335–337.

*Primary Examiner*—Johnnie R. Brown
*Assistant Examiner*—Elli Peselev
*Attorney, Agent, or Firm*—Larson and Taylor

[57] ABSTRACT

As new compounds are now provided 14-O-(3,4-disubstituted benzoyl)adriamycins which are of low cytotoxicity and exhibit a high activity inhibitory to the reverse transcriptase of human immunodeficiency virus (HIV) and which can inhibit propagation of HIV.

12 Claims, No Drawings 5,003,055

ANTHRACYCLINE DERIVATIVES HAVING INHIBITORY ACTIVITY AGAINST REVERSE TRANSCRIPTASE OF HUMAN IMMUNODEFICIENCY VIRUS

SUMMARY OF THE INVENTION

This invention relates to novel compounds which are anthracycline derivatives, namely, 14-O-acyladriamycin derivatives having such activity that inhibits the reverse transcriptase of human immunodeficiency virus (hereinafter abbreviated as "HIV").

BACKGROUND OF THE INVENTION

HIV which is a causative agent for acquired immune deficiency syndromes (usually called AIDS) is a retro virus, and to discover such a chemical compound or substance which can inhibit the reverse transcriptase of HIV is considered to be one of the targets for the discovery of an anti-HIV substance. Adriamycin and other certain compounds have already been known to inhibit the reverse transcriptase of fowl leukemia virus {"Journal of Antibiotics" 40, 396–399 (1987)}, but they can exhibit high toxicity. There is thus a strong demand for the preparation and development of a novel adriamycin derivative which has a high inhibitory activity against the reverse transcriptase of HIV but shows a low cytotoxicity.

We, the present inventors, have carried out an investigation so as to meet the above-described demand. We have synthetically prepared a variety of anthracycline derivatives by using the hydrobromide or hydrochloride of 14-bromodaunomycin (Belgian Patent No. 731398 issued at Oct. 13, 1969) or 14-chlorodaunomycin (Japanese Patent Application No. 173924/87, U.S. application Ser. No. 07/ 204,363; European patent application No. 88305309.2) as a starting material. As a result, we have succeeded in preparing such 14-O-acyladriamycin derivatives represented by the under-mentioned general formula (I). Moreover, it has also been found that these novel compounds have strong inhibitory activity against the reverse transcriptase of HIV and are of low cytotoxicity, leading to completion of this invention.

DETAILED DESCRIPTION OF THE INVENTION

In a first aspect of this invention, there is thus provided, as a novel compound, an anthracycline derivative having the general formula (I):

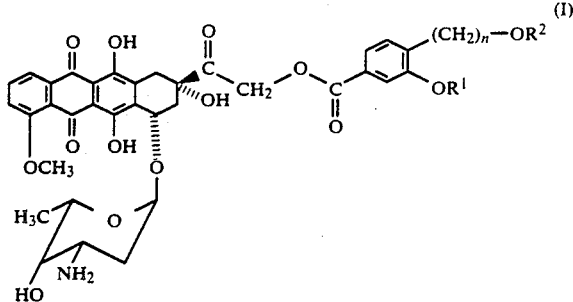

wherein $R^1$ and $R^2$ are the same or different and each denote a hydrogen atom or a substituted or unsubstituted straight or branched alkyl group of 1 to 18 carbon atoms, a substituted or unsubstituted aralkyl group or a substituted or unsubstituted aryl group or an acyl group, or $R^1$ and $R^2$ taken together form an optionally substituted straight or branched alkylene group of 1 to 6 carbon atoms, an optionally substituted alkylidene group 2 to 6 carbon atoms or an optionally substituted cycloalkylidene group of 3 to 6 carbon atoms, and n is an integer of 0 or 1, or an acid addition salt thereof. According to a particular embodiment of the first aspect of this invention, there is provided as new compounds, a 14-O-(3,4-disubstituted)benzoyladriamycin, namely an anthracycline derivative having the formula (Ia):

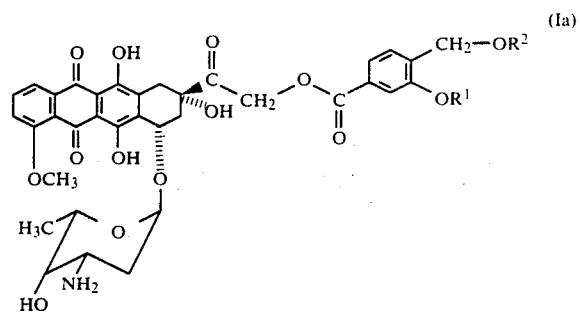

wherein $R^1$ and $R^2$ are the same or different and each denote a hydrogen atom or a substituted or unsubstituted straight or branched alkyl group of 1 to 18 carbon atoms, a substituted or unsubstituted aralkyl group or a substituted or unsubstituted aryl group, or $R^1$ and $R^2$ taken together form an optionally substituted straight or branched alkylene group of 1 to 6 carbon atoms, an optionally substituted alkylidene group of 2 to 6 carbon atoms or an optionally substituted cycloalkylidene group of 3 to 6 carbon atoms, or an acid addition salt thereof. According to another embodiment, there is further provided a 14-O-(3,4-dialkoxy)benzoyladriamycin or 14-O-(3,4-di-alkanoyloxy or 3,4-di-aroyloy)benzoyladriamycin, namely an anthracycline derivative having the formula (Ib):

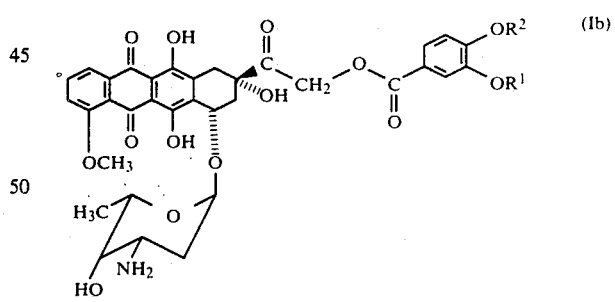

wherein $R^1$ and $R^2$ are the same and each denote a hydrogen atom or a substituted or unsubstituted straight or branched alkyl group of 1 to 18 carbon atom, a substituted or unsubstituted aralkyl group, a substituted or unsubstituted aryl group or an acyl group, or an acid addition salt thereof.

Where $R^1$ or $R^2$ is an alkyl group in the compound of the general formula (I) according to this invention, the alkyl group may preferably be a $C_{1-18}$ alkyl group such as methyl, ethyl, n-propyl, isopropyl, n-butyl, isobutyl, tert-butyl, n-hexyl, n-undecyl and n-octa-decyl. This invention also embraces compounds of the formula (I) in which $R^1$ and $R^2$ are each a cycloalkyl group such as cyclohexyl. Further, $R^1$ and $R^2$ may individually be an aralkyl group such as benzyl and phenethyl, or an aryl group such as phenyl and naphthyl. Where $R^1$ or $R^2$ is an alkyl, aralkyl or aryl group, it may bear one or more lower ($C_1$–$C_6$) alkoxy groups, hydroxyl groups, halogen atoms and/or the like as the substituents thereon.

When n is 1 in the compound of the formula (I), $R^1$

Next, certain exemplary compounds of the general formula (I) according to this invention are summarized in Table 1-a and Table 1-b. The specific rotations and melting points of the individual compounds are also shown. The abbreviated compound names given in Table 1-a and Table 1-b will be referred to hereinafter.

TABLE 1-a

| Compound No. (Example No.) | Compound abbreviation | General formula (I) | | | Melting point (°C.) |
|---|---|---|---|---|---|
| | | n | $R^1$ | $R^2$ | Optical rotation | |
| 1 (Example No. 1) | NOVA-1 | 1 | —$CH_3$ | —$CH_3$ | $[\alpha]_D^{27}$ +260° (c 0.01, $CH_3OH$) | 143–163 |
| 2 (Example No. 2) | NOVA-2 | 1 | —$C_6H_{13}$-n | —$C_6H_{13}$-n | $[\alpha]_D^{26}$ +180° (c 0.01, $CH_3OH$) | 110–142 |
| 3 (Example No. 3) | NOVA-3 | 1 | —$C_{11}H_{23}$-n | —$C_{11}H_{23}$-n | $[\alpha]_D^{28}$ +170° (c 0.01, $CHCl_3$) (as hydrochloride) | 160–169 (as hydrochloride) |
| 4 (Example No. 4) | NOVA-4 | 1 | —$C_{11}H_{23}$-n | —H | $[\alpha]_D^{27}$ +190° (c 0.01, $CH_3OH$) | 110–126 |
| 5 (Example No. 5) | NOVA-5 | 1 | —$C_{18}H_{37}$-n | —$C_{18}H_{37}$-n | $[\alpha]_D^{26}$ +230° (c 0.01, $CHCl_3$) (as hydrochloride) | 167–174 (as hydrochloride) |
| 6 (Example No. 6) | NOVA-6 | 1 | —H | —H | $[\alpha]_D^{27}$ +150° (c 0.01, $CH_3OH$) | Gradual decomposition (no definite melting point) |
| 7 (Example No. 7) | NOVA-7 | 1 | \C(CH_3)(CH_3)/ | | $[\alpha]_D^{27}$ +230° (c 0.01, $CH_3OH$) | 195–202 |

TABLE 1-b

| Compound No. (Example No.) | Compound abbreviation | General Formula (I) | | | Melting point (°C.) |
|---|---|---|---|---|---|
| | | n | $R^1$ | $R^2$ | Optical rotation | |
| 8 (Example No. 8) | NOVA-8 | 0 | —$CH_3$ | —$CH_3$ | $[\alpha]_D^{26}$ +320° (c 0.01, $CH_3OH$) | 188–189 |
| 9 (Example No. 9) | NOVA-9 | 0 | —$C_6H_{13}$-n | —$C_6H_{13}$-n | $[\alpha]_D^{25}$ +220° (c 0.01, $CHCl_3$) | 167–170 |
| 10 (Example No. 10) | NOVA-10 | 0 | —$C_{11}H_{23}$-n | —$C_{11}H_{23}$-n | $[\alpha]_D^{24}$ +170° (c 0.01, $CHCl_3$—$CH_3OH$ (1:1)) (as hydrochloride) | 185–189 (as hydrochloride) |
| 11 (Example No. 11) | NOVA-11 | 0 | —$C_{18}H_{37}$-n | —$C_{18}H_{37}$-n | $[\alpha]_D^{23}$ +150° (c 0.01, $CHCl_3$) (as hydrochloride) | 154 (as hydrochloride) |
| 12 (Example No. 12) | NOVA-12 | 0 | —$COC_4H_9$ | —$COC_4H_9$ | $[\alpha]_D^{23}$ +190° (c 0.01, $CH_3OH$) (as hydrochloride) | 176–178 (as hydrochloride) | and $R^2$ may also be coupled together, thereby forming an alkylene group of 1-6 carbon atoms such as methylene, ethylene, propylene or isopropylene group; an alkylidene group of 2-6 carbon atoms such as isopropylidene group; or a cycloalkylidene of 3-6 carbon atoms such as cyclohexylidene group. Such a group may again bear one or more hydroxyl groups, halogen atoms and/or the like as the substituents thereon.

$R^1$ and $R^2$ may each be an acyl group, including an alkanoyl group of 2 to 6 carbon atoms such as acetyl, propionyl and valeryl, as well as an aroyl group such as benzoyl, when n is zero in the compound of the formula (I).

Where the compound of the formula (I) of this invention is in the form of an acid addition salt thereof, the acid may be a pharmaceutically acceptable inorganic acid such as hydrochloric acid, sulfuric acid and phosphoric acid; or a pharmaceutically acceptable organic acid such as acetic acid, propionic acid, malic acid, citric acid and methanesulfonic acid.

Physiological and biological properties of the novel anthracycline derivatives of general formula (I) according to this invention will hereinafter be described. The above exemplified compounds of this invention are all reddish powder or crystalline powder. Results of mass spectroscopy and Rf value measurement (silica gel thin-layer chromatography) of the individual compounds will be summarized in Table 3-a and Table 3-b, which will appear after Examples 1-7 given hereinafter, where the preparation of these exemplary compounds are illustrated.

Description will next be made of evaluation tests for the HIV reverse transcriptase-inhibitory activity and the cytotoxicity of the novel anthracycline derivatives of the general formula (I) according to this invention.

(a) After treating a supernatant of a culture of HIV-infected T4-cells (Molt 4/HTLV 1116/H9) with 9.5% polyethylene glycol for 3 hours, the supernatant was centrifuged at 2500 rpm for 30 minutes to obtain a precipitate. This precipitate was lysed with a mixture comprising 33.3% glycerol, 16.7 m tris-HCl (pH 7.5), 533 mM KCl, 0.32% Triton X-100 and 3.3 mM dithiothreitol, so as to prepare an HIV lysate ($2.5 \times 10^6$ PFU/ml) The activity of the reverse transcriptase present in the HIV lysate thus prepared was determined in terms of the up-take rate of [$\alpha$-$^{32}$P]dATP during the synthesis of DNA, with using rabbit-$\beta$-globin mRNA and oligo dT as the template and primer, respectively. Thus, 1 $\mu$l of the HIV lysate was added to 9 $\mu$l of an enzymatic reaction solution comprising 50 mM tris-HCl (pH 8.3), 70 mM KCl, 10 mM MgCl$_2$, 30 mM mercaptoethanol, 90 nM dNTPs, 3.3 $\mu$g/ml oligo dT, 8.3 mU/ml human placenta RNase inhibitor, 5 $\mu$g/ml $\beta$-globin mRNA, 0.14 mCi/ml [$\alpha$-$^{32}$P]dATP. After incubating the resultant mixture at 37° C. for 30 minutes, 10% aqueous trichloroacetic acid (TCA) was added to terminate the reaction.

After completion of the reaction, the whole reaction mixture was placed on a nitrocellulose membrane filter so as to adsorb the resultant DNA into the filter. The filter was then washed with 5% TCA and 20 mM sodium pyrophosphate to remove the unreacted [$\alpha$-$^{32}$P]dATP therefrom. The amount of the resultant DNA on the nitrocellulose membrane filter was calculated by measuring its radioactivity.

The novel anthracycline derivatives of this invention were separately added to the enzymatic reaction solution. The above experiment was repeated using the so prepared enzymatic reaction solution containing the anthracycline derivative as a test compound, so that the evaluation was made of IC$_{50}$ of the test compound inhibitory to the activity of the HIV reverse transcriptase, namely the concentration of the test compound which was 50% inhibitory to the activity of the HIV reverse transcriptase. Results are shown in Table 2, in comparison with that of adriamycin (abbreviated as "ADM") as a reference compound.

(b) On the other hand, the cytotoxicity was measured in the following manner. The novel anthracycline derivative of this invention was added to $5 \times 10^3$ cells of mouse lymphocytic leukemia P-388 in an incubation medium. After stirring, themixture was incubated Forty-eight hours later, the rate (%) of proliferation of the cells was measured by the MTT technique. IC$_{50}$ values of the novel anthracycline derivatives of this invention inhibitory to the proliferation of the P-388 cells are shown in Table 2, in comparison with that of adriamycin (ADM) as a reference compound.

In addition, the ratio of the HIV reverse transcriptase inhibitory activity to the cytotoxicity of each novel anthracycline derivative of this invention is also shown in Table 2, in comparison with that of ADM.

TABLE 2

| Abbreviation of test compounds | HIV reverse transcriptase inhibitory activity (IC$_{50}$, $\mu$g/ml) (A) | Cytotoxicity against P-388 cells (IC$_{50}$, $\mu$g/ml) (B) | Enzyme inhibitory activity/cytotoxicity ratio (A)/(B) |
|---|---|---|---|
| ADM (Comparative) | 55 | 0.037 | 1500 |
| ADM.HCl (Comparative) | 43.5;35 | 0.02 | 2175;1750 |
| NOVA-1 (This invention) | 30 | 0.29 | 103 |
| NOVA-2 (This invention) | 17 | 0.48 | 35 |
| NOVA-3.HCl (This invention) | 18.5 | 0.49 | 38 |
| NOVA-4 (This invention) | 12.5 | 0.5 | 25 |
| NOVA-5.HCl (This invention) | 22 | 3.2 | 6.9 |
| NOVA-6 (This invention) | 55 | 0.15 | 370 |
| NOVA-7 (This invention) | 23 | 0.19 | 121 |
| NOVA-8 (This invention) | 19 | 0.33 | 58 |
| NOVA-9 (This invention) | 20 | 2.6 | 7.8 |
| NOVA-9.HCl (This invention) | 15 | 3.1 | 4.8 |
| NOVA-9.½H$_2$SO$_4$ (This invention) | 23 | 5.2 | 4.4 |
| NOVA-10.HCl (This invention) | 16 | 1.8 | 8.9 |
| NOVA-11.HCl (This invention) | 100 | 1.9 | 53 |
| NOVA-12.HCl (This invention) | 11 | 0.22 | 50 |

As is apparent from the results shown in Table 2 above, the new compounds of the general formula (I) according to this invention are able to exhibit an activity inhibitory to HIV reverse transcriptase and hence have an activity inhibitory to the HIV proliferation. In addition, they also have an antitumor activity as they show an inhibitory activity against the proliferation of lymphocytic leukemia cells P-388.

Preparation of a 14-O-acyladriamycin derivative of the general formula (I) according to this invention can be conducted by reacting 14-bromodaunomycin hydrobromide or 14-chlorodaunomycin hydrochloride with a metal salt (preferably an alkali metal salt such as the sodium salt, potassium salt or the like) of a benzoic acid derivative having the general formula (II):

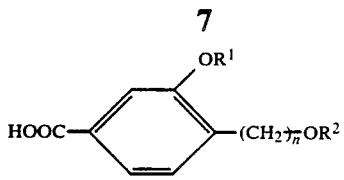

(II)

wherein $R^1$ and $R^2$ have the same meanings as defined above and n is 0 or 1. Upon isolation and purification by chromatographic method as needed, the 14-acyladriamycin derivative of the general formula (I) can be obtained as its pure product. In a second aspect of this invention, there is provided a process for the preparation of the anthracycline derivative of the formula (I) according to this invention, which comprises reacting a metal salt of a 3,4-disubstituted benzoic acid derivative having the general formula (II)

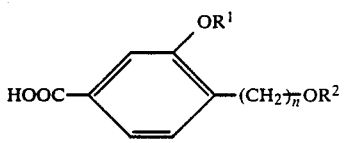

(II)

wherein $R^1$ and $R^2$ are the same or different and each denote a hydrogen atom or an optionally substituted straight or branched alkyl group of 1 to 18 carbon atoms, an optionally substituted aralkyl group( an optionally substituted aryl group or an acyl group, or $R^1$ and $R^2$ taken together form an optionally substituted straight or branched alkylene group of 1 to 6 carbon atoms, an optionally substituted alkylidene group of 2 to 6 carbon atoms or an optionally substituted cycloalkylidene group of 3 to 6 carbon atoms, and n is an integer of 0 or 1, with a 14-halo-daunomycin having the formula (III):

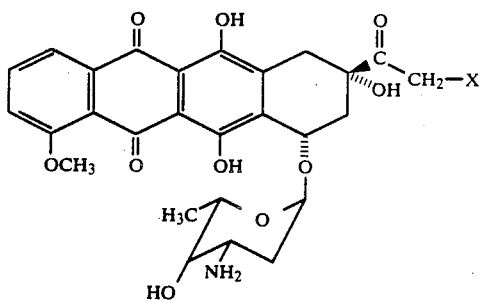

(III)

wherein X is a bromine or chlorine atom, or an acid addition salt thereof, in an inert organic solvent to produce the compound of the formula (I).

In the process of this invention, the compound of the formula (II) may be used in a stoichiometric proportion or in a slight excess to the 14-O-halodaunomycin of the formula (III). The organic solvent where the reaction is carried out may be a dry lower alkanol such as methanol and ethanol, chloroform and their mixture.

The reaction may be effected at ambient temperature or at an elevated temperature, and generally the reaction temperature may preferably be in a range of 10° C. to 50° C.

Where the benzoic acid derivative of the general formula (II) is a 3,4-di-substituted benzoic acid derivactive of the formula (II) wherein $R^1$ and $R^2$ are individually an alkyl, aralkyl or aryl group and n is 0 or 1, the compound can be prepared as a corresponding O-alkyl-, O-aralkyl- or O-aryl derivative, by condensing known 3-hydroxy-4-hydroxymethyl benzoic acid (Japanese Patent Application first publication "Kokai" No. 13238/80 published Jan. 30, 1980) or known 3,4-dihydroxybenzoic acid (namely, protocatechuic acid) with a corresponding alkyl halide, aralkyl halide or aryl halide in the presence of a base, for example, a metal base such as sodium hydride or potassium hydride, or an organic base such as diisopropylethylamine in an organic solvent.

Where the $R^1$ and $R^2$ are coupled together to form a single alkylene, alkylidene or cycloalkylidene group in the compound of the general formula (II) where n is 1, the compound can be prepared by reacting 3-hydroxy-4-hydroxymethylbenzoic acid either with an alkylene dihalide of the formula X-R'-X, where R' is an alkylene group and X is a chlorine or bromine atom, or with a 1,1-or 2,2-dimethoxyalkane or with a 1,1-dimethoxycycloalkane.

The above compound of general formula (II) where n is 1 is also a novel compound which is important as an intermediate for the synthesis of the 14-O-acyladriamycin derivatives according to the first aspect of this invention.

In a third aspect of this invention, therefore, there is provided a 3,4-disubstituted benzoic acid derivative having the general formula (IIa)

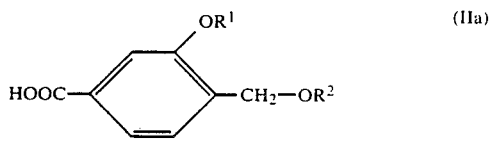

(IIa)

wherein $R^1$ and $R^2$ are the same or different and each denote a hydrogen atom or an optionally substituted straight or branched alkyl group of 1 to 18 carbon atoms, an optionally substituted aralkyl group, or an optionally substituted aryl group, or $R^1$ and $R^2$ taken together form an optionally substituted straight or branched alkylene group of 1 to 6 carbon atoms, an optionally substituted alkylidene group of 2 to 6 carbon atoms or an optionally substituted cycloalkylidene group of 3 to 6 carbon atoms, or its metal salt. The metal salt of the compound of the formula (IIa) may preferably be such salt with an alkali metal such as sodium and potassium or an alkaline earth metal such as calcium and magnesium.

Suitable examples of the new compound of the general foumula (IIa) according to the third aspect of this invention include 3-methoxy-4-methoxymethylbenzoic acid, 3-n-hexyloxy-4-n-hexyloxymethylbenzoic acid, 3-n-undecyloxy--b 4-n-undecyloxymethylbenzoic acid, 4-hydroxymethyl-3-n-undecyloxybenzoic acid, 3-n-octadecyloxy-4-n-octadecyloxymethylbenzonic acid, 3,4-0-isopropylidene-3-hydroxy-4-hydroxymethylbenzoic acid and 3,4-0-cyclohexylidene-3-hydroxy-4-hydroxymethylbenzoic acid as well as their metal salts. Among these metal salts, alkali metal salts and alkaline earth metal salts are preferred.

The first aspect of this invention will next be illustrated with reference to Examples 1-12.

EXAMPLE 1:

Preparation of 14-O-(3-methoxy-4-methoxymethylbenzoyl)adriamycin (NOVA-1)

Sodium 3-methoxy-4-methoxymethylbenzoate which had been prepared from 66.2 mg of 3-methoxy-4-methoxymethylbenzoic acid was dissolved in 12 ml of anhydrous methanol Then, 160 mg of 14-bromodaunomycin hydrobromide (hereinafter abbreviated as "14-Br-DM.HBr") was dissolved into the methanolic solution, followed by heating the resultant solution at 40° C. for 4 hours. The reaction solution was purified by preparative thin layer chromatography {developer: chloroform-methanol-concentrated aqueous ammonia (90:20:1)}, thereby obtaining 43.8 mg of the titled compound (NOVA-1) as a dark reddish solid.

EXAMPLE 2:

Preparation of 14-O-(3-n-hexyloxy-4-n-hexyloxymethylbenzoyl)adriamycin (NOVA-2)

In 2.8 ml of anhydrous methanol were dissolved 57.0 mg of 14-Br-DM·HBr and sodim 3-n-hexyloxy04-n-hexyloxymethylbenzoate which had been prepared from 55.8 mg of 3-n-hexyloxy-4-n-hexyloxymethylbenzoic acid. The reaction mixture was left over for 24 hours at room temperature. The reaction solution obtained was purified by preparative thin layer chromatography {developer: chloroform-methanolconcentrated aqueous ammonia (90:30:1)}, thereby obtaining 23.7 mg of the titled compound (NOVA-2) as a dark reddish solid.

EXAMPLE 3:

Preparation of 14-O-(3-n-undecyloxy-4-n-undecyloxymethylbenzoyl)adriamycin hydrochloride (NOVA-3 hydrochloride)

Sodium 3-n-undecyloxy-4-n-undecyloxymethylbenzoate which had been prepared from 40.0 mg of 3-n-undecyloxy-4-n-undecyloxymethylbenzoic acid was dissolved in 1.7 ml of anhydrous methanol. Then, 57.7 mg of 14-Br-DM HBr was dissolved into the methanolic solution, and the resultant mixture was allowed to stand for 7 hours at room temperature. Anhydrous methanol (1.7 ml) and chloroform (1.7 ml) were added further to form a homogeneous solution. The solution was stirred for 24 hours at room temperature, followed by heating the solution at 40° C. for 4 hours.

The reaction solution obtained was concentrated under reduced pressure, and the residue was purified by preparative thin layer chromatography {developer: chloroform-methanolconcentrated aqueous ammonia (90:20:1)} to give 26.5 mg of NOVA-3 as a dark reddish solid. Chloroform (1.0 ml) and methanol (1.0 ml) were added to the compound to dissolve same, followed by addition of 26.4 μl of 1.0 N hydrochloric acid to the solution. While adding isopropyl ether further, the reaction solution was concentrated under reduced pressure. The residue was dried completely to afford 27.4 mg of NOVA-3 hydrochloride.

EXAMPLE 4:

Preparation of 14-O-(3-n-undecyloxy-4-hydroxymethylbenzoyl)adriamycin (NOVA-4)

Sodium 4-hydroxymethyl-3-n-undecyloxybenzoate which had been prepared from 31.0 mg of 4-hydroxymethyl-3-n-undecyloxybenzoic acid was dissolved in 1.3 ml of anhydrous methanol. Then, 66.1 mg of 14-Br-DM.HBr was dissolved in the methanolic solution, followed by heating the resultant solution at 30° C. for 24 hours. The reaction solution obtained was purified by preparative thin layer chromatography {developer: chloroform-methanol-concentrated aqueous ammonia (90:20:1)} to obtain 23.3 mg of NOVA-4 as a dark reddish solid.

EXAMPLE 5:

Preparation of 14-O-(3-n-octadecyloxy-4-n-octadecyloxymethylbenzoyl)adriamycin hydrochloride (NOVA-5 hydrochloride)

Anhydrous methanol (1.0 ml) and chloroform (1.0 ml) were added to 21.2 mg of 14-Br-DM.HBr and sodium 3-n-octadecyloxy-4-n-octadecyloxymethylbenzoate which had been prepared from 20.8 mg of 3-n-octadecyloxy-4-n-octadecyloxymethylbenzoic acid, thereby dissolving the latter compounds. After allowing the reaction mixture to stand at room temperature for 90 minutes, 4.6 mg of sodium iodide was added. The resultant mixture was left over at room temperature for 24 hours and then heated at 40° C. for 2 hours.

The reaction solution obtained was concentrated under reduced pressure, and the residue was purified by preparative thin layer chromatopraphy {developer: chloroformmethanol-concentrated aqueous ammonia (90:10:1)} to give 7.0 mg of NOVA-5 as a dark reddish solid. Chloroform (0.5 ml) and ethanol (1.5 ml) were added to the compound to dissolve same, followed by addition of 5.8 μl of 1.0 N hydrochloric acid. After concentrating the resulting mixture under reduced pressure, the residue was dried thoroughly to afford 7.2 mg of NOVA-5 hydrochloride.

EXAMPLE 6:

Preparation of 14-O-(3-hydroxy-4-hydroxymethylbenzoyl)adriamycin (NOVA-6)

Anhydrous methanol (10 ml) was added to 200 mg of 14-Br-DM.HBr and sodium 3-hydroxy-4-hydroxymethylbenzoate which had been prepared from 97.9 mg of 3-hydroxy-4-hydroxymethylbenzoic acid, whereby the latter compounds were suspended in the methanol. The suspension obtained was irradiated with ultrasonic waves to disintegrate the insoluble matter and was then stirred overnight at room temperature.

The insoluble matter was filtered off and then washed with methanol. The filtrate and washing were combined and concentrated under reduced pressure. The residue was purified by silica gel chromatography {developer: chloroform-methanol-concentrated aqueous ammonia (90:20:3)}. Fractions of the eluate containing the target product were concentrated under reduced pressure while adding ethanol thereto. Methanol and isopropyl ether were added successively to the residue, followed by concentration under reduced pressure to yield 74.4 mg of NOVA-6 as a dark reddish solid.

EXAMPLE 7:

Preparation of 14-O-(0-isopropylidene-3-hydroxy4-hydroxymethyl-benzoyl)adriamycin (NOVA-7)

Anhydrous methanol (8.4 ml) was added to sodium 0-isopropylidene-3-hydroxy-4-hydroxymethylbenzoate which had been prepared from 50.7 mg of 0-isopropylidene-3-hydroxy-4-hydroxymethylbenzoic acid, so that the sodium salt was dissolved. Thereafter, 116 mg of 14-Br-DM.HBr was added to the resulting methanolic solution, and the resultant mixture was heated at 40° C. for 5 hours.

The reaction solution was concentrated under reduced pressure until its volume was reduced to about one half of the original volume, followed by purification by preparative thin layer chromatography {developer: chloroform-methanol-concentrated aqueous ammonia (90:20:1)} to give 31.3 mg of the titled compound (NOVA-7) as a dark reddish solid.

EXAMPLE 8:

Preparation of 14-O-(3,4-dimethoxybenzoyl)-adriamycin (NOVA-8)

Anhydrous methanol (3.8 ml) was added to sodium 3,4-dimethoxybenzoate, which had been prepared from 40.8 mg of 3,4-dimethyoxybenzoic acid, and 76.9 mg of 14-Br-DM.HBr to form the mixture as a suspension. The suspension was stirred at room temperature for 48 hours and then at 40° C for 24 hours. The reaction solution was purified by preparative thin layer chromatography {developer: chloroformmethanol-concentrated aqueous ammonia (90:20:1)}, thereby affording 15.7 mg of the titled compound (NOVA-8) as a reddish solid.

EXAMPLE 9:

Preparation of 14-O-(3,4-di-n-hexyloxybenzoyl)adriamycin (NOVA-9)

Anhydrous methanol (2.6 ml) was added to sodium 3,4-di-n-hexyloxybenzoate, which had been prepared from 48.0 mg of 3,4-di-n-hexyloxybenzoic acid, and 51.2 mg of 14-Br-DM.HBr, followed by stirring the resultant mixture at room temperature for 24 hours. Chloroform (1.3 ml) was then added, followed by stirring the mixture at room temperature for further 24 hours. The reaction solution obtained was purified by preparative thin layer chromatography {developer: chloroform-methanol-concentrated aqueous ammonia (90:20:1)}, thereby yielding 23.1 mg of the titled compound (NOVA-9) as a reddish solid.

Then, 2.0 mg of the titled compound (the free base) was dissolved in a mixture of 1.0 ml of chloroform and 1.0 ml of methanol, followed by addition of 2.4 µl of 1.0 N hydrochloric acid. The resultant mixture was concentrated under reduced pressure, and the residue was dried thoroughly to give 2.1 mg of the hydrochloride of the titled compound. On the other hand, 2.4 µl of 1.0 N sulfuric acid was added to the solution of 2.0 mg of the free base compound dissolved in the chloroform-methanol solvents. The resultant mixture was concentrated under reduced pressure, and the residue was dried thoroughly to give 2.1 mg of the ½ sulfate of the titled compound.

EXAMPLE 10:

Preparation of 14-O-(3,4-di-n-undecyloxybenzoyl)adriamccin (NOVA-10)

Anhydrous methanol (1.0 ml) and chloroform (1.0 ml) were successively added to tetramethylammonium 3,4-di-n-undecyloxybenzoate, which had been prepared from 14.4 mg of 3,4-di-n-undecyloxybenzoic acid, and 29.0 mg of 14-Br-DM.HBr. Afer allowing the resultant mixture to stand at room temperature for 24 hours, the deposited insoluble matter was disintegrated by ultrasonic waves. The reaction solution was purified by preparative thin layer chromatography {developer: chloroform-methanol-concentrated aqueous ammonia (90:20:1)}, thereby obtaining 6.3 mg of the titled compound (NOVA-10) as a reddish solid.

Then, 5.3 mg of the titled compound (the free base) was dissolved in 1.3 ml of chloroform and 4.0 ml of methanol followed by addition of 5.4 µl of 1.0 N hydrochloric acid. The resultant mixture was concentrated under reduced pressure, and the residue was dried thoroughly to give 5.5 mg of the hydrochloride of the titled compound.

EXAMPLE 11:

Preparation of 14-O-(3 4-di-n-octadecyloxybenzoyl)adriamycin (NOVA-11)

Anhydrous methanol (2.0 ml) and chloroform (2.0 ml) were added to sodium 3,4-di-n-octadecyloxybenzoate which had been prepared from 37.3 mg of 3,4-di-n-octadecyloxybenzoic acid. The resultant mixture was heated to dissolve the sodium salt. Thereafter, 60.0 mg of 14-Br-DM.HBr and 198 mg of sodium iodide were added, followed by addition of 4.0 ml of anhydrous dimethylformamide. After stirring the reaction mixture at 40° C. for 24 hours, the resulting reaction solution was concentrated under reduced pressure. The residue was extracted wihh 150 ml of chloroform. The extract was washed with 20 ml of water and then dried over anhydrous sodium sulfate. The solution in chloroform was concentrated under reduced pressure, and the residue was purified by preparative thin layer chromatography {developer: chloroform-methanol-concentrated aqueous ammonia (90:20:1)}, thereby affording 3.2 mg of the titled compound (NOVA-11) as a reddish solid.

Methanol (2.9 ml), 1.0 N hydrochloric acid (2.4 µl) and chloroform (1.7 ml) were successively added to 2.9 mg of the titled compound (the free base). The resultant mixture was heated to dissolve the free base compound. The resultant solution was concentrated under reduced pressure, and the residue was dried thoroughly to give 3.0 mg of the hydrochloride of the titled compound.

EXAMPLE 12:

Preparation of 14-O-(3,4-di-n-valeryloxybenzoyl)adriamycin (NOVA-12)

Anhydrous methanol (2.5 ml) and chloroform (1.0 ml) were added to sodium 3,4-di-n-valeryloxybenzoate which had been prepared from 18.1 mg of 3,4-di-n-valeryloxybenzoic acid, and 50.0 mg of 14-Br-DM.HBr so as to dissolve the sodium salt and hydrobromide into the solvents. After allowing the reaction mixture to stand at room temperature for 24 hours, the resulting reaction solution was purified by preparative thin layer chromatography {developer: chloroform-methanol-concentrated aqueous ammonia (90:20:1)} to give 7.4 mg of the titled compound (NOVA-12) as a reddish solid.

Methanol (3.7 ml) and 1.0 N hydrochloric acid (8.7 μl) were added to 7.4 mg of the titled compound (the free base) so as to dissolve the free base. The resultant mixture was concentrated under reduced pressure, and the residue was dried thoroughly to obtain 7.7 mg of the hydrochloride of the titled compound.

Mass spectroscopic data of the comopunds obtained is Examples 1–12 and their Rf values as determined by silica gel thin layer chromatogrzphy are summarized below in Table 3.

TABLE 3

| Abbreviation of compound of this invention | Mass Spectroscopic datum | Rf value {chloroform-methanol concentrated aqueous ammonia (90:20:1)} |
| --- | --- | --- |
| NOVA-1 | 722 (MH+) | 0.61 |
| NOVA-2 | 862 (MH+) | 0.67 |
| NOVA-3 | 1002 (MH+) | 0.72 |
| NOVA-4 | 848 (MH+) | 0.61 |
| NOVA-5 | 1198 (MH+) | 0.78 |
| NOVA-6 | 693 (M+) | 0.32 |
| NOVA-7 | 734 (MH+) | 0.61 |
| NOVA-8 | 707 (M+) | 0.61 |
| NOVA-9 | 847 (M+) | 0.67 |
| NOVA-10 | 988 (MH+) | 0.72 |
| NOVA-11 | 1184 (MH+) | 0.78 |
| NOVA-12 | 848 (MH+) | 0.65 |

Now, the preparation of some examples of the new compound, the 3,4-disubstituted benzoic acid derivative of the formula (IIa) according to the third aspect of this invention is illustrated with reference to the following Examples 13–20. The product compounds of these Examples 13–20 were used in the Examples 1–7 above, respectively.

EXAMPLE 13:

Preparation of 3-methoxy-4-methoxymethylbenzoic acid

Anhydrous dimethylformamide (10 ml) was added to 100 mg of sodium 3-hydroxy-4-hydroxymethylbenzoate and 84 mg of 60% sodium hydride in oil, followed by addition of 0.13 ml of methyl iodide. The resultant mixture was then stirred at room temperature for 7 hours to conduct the methylation of the benzoate compound. After adding 4.0 ml of water and heating the resultant reaction solution at 50° C. for 24 hours, 2.6 ml of a 1.0 N aqueous solution of sodium hydroxide was added, followed by heating the resultant mixture at 50° C. for 5 hours.

The reaction solution as formed was concentrated under reduced pressure, and the residue was extracted with 20 ml of water, followed by addition of a 5% aqueous solution of sodium hydrogen sulfide to adjust the pH to 1. The resultant mixture was extracted twice with 20 ml of chloroform. The chloroform layers were combined, dried over anhydrous sodium sulfate and then concentrated under reduced pressure. The residue obtained was purified by preparative thin layer chromatography {developer: chloroform-mehtanol (8:1)} to give 66.2 mg of 3-methoxy-4-methoxymethylbenzoic acid as a white solid. Melting point: 160–163° C. EIMS: m/z 196 (M+).

EXAMPLE 14:

Preparation of 3-n-hexyloxy-4-n-hexyloxymethylbenzoic acid

Anhydrous dimethylformamide (10 ml) was added to 100 mg of 3-hydroxy-4-hydroxymethylbenzoic acid and 95.2 mg of sodium hydride in oil, followed by addition of 0.33 ml of n-hexyl bromide. The resultant mixture was then stirred at room temperature for 24 hours. n-Hexyl bromide (0.10 ml) was then added, and the resultant mixture was stirred at room temperature for 24 hours to effect the alkylation reaction.

The resulting reaction solution was then added dropwise to 100 ml of a 5% aqueous solution of potassium hydrogen sulfate, followed by extraction with 100 ml of chloroform. The chloroform layer was washed with water, dried over anhydrous sodium sulfate and then concentrated under reduced pressure. Tetrahydrofuran (10 ml), a 10% aqueous solution of sodium hydroxide (2.0 ml) and methanol (4.0 ml) were added successively to the resultant residue to dissolve the latter. The solution obtained was left over at room temperature for 24 hours.

The resulting reaction solution was concentrated under reduced pressure, and the residue was extracted with 100 ml of chloroform. The extract was washed successively with a 5% aqueous solution of potassium hydrogen sulfate and water, and then dried over anhydrous sodium sulfate. The solution was concentrated under reduced pressure. The residue was purified by chromatography on a silica gel column {gradiently developed with chloroform →chloroform-ethanol (50:1)} to give 89.6 mg of 3-n-hexyloxy-4-n-hexyloxymethylbenzoic acid as pale yellowish needles (which were in the crystalline form in refrigerator but became an oil at room temperature). EIMS: m/z 336 (M+).

EXAMPLE 15:

Preparation of methyl 3-n-undecyloxy-4-n-undecyloxymethylbenzoate and methyl 4-hydroxymethyl-3-n-undecyloxybenzoate Anhydrous dimethylformamide (10 ml) was added to 100 mg of methyl 3-hydroxy-4-hydroxymethylbenzoate and 343 mg of 60% sodium hydride in oil, to form a mixture as a suspension. n-Undecyl iodide (0.32 ml) was further added, and the resultant mixture was stirred at room temperature for 24 hours.

The resulting reaction solution was then added dropwise to 100 ml of a 5% aqueous solution of potassium hydrogen sulfate, followed by extraction with 100 ml of chloroform. The chloroform layer was washed with water, dried over anhydrous sodium sulfate and then concentrated under reduced pressure The residue was purified by chromatography on a silica gel column {gradiently developed with chloroform-n-hexane (1:1 →2:1)}, to give 44.4 mg of methyl 3-n-undecyloxy-4-n-undecyloxymethylbenzoate as a colorless oil and 83.0 mg of methyl 4-hydroxymethyl-3-n-undecyloxybenzoate as a pale yellowish syrup.

EXAMPLE 16:

Preparation of 3-n-undecyloxy-4-n-undecyloxymethylbenzoic acid

Tetrahydrofuran (2.0 ml), a 10% aqueous solution of sodium hydroxide (0.40 ml) and methanol (2.0 ml) were successively added to 44.4 mg of methyl 3-n- undecyloxy-4-undecyloxymethylbenzoate to dissolve the latter compound. The resultant solution was left over at room temperature for 24 hours.

The resulting reaction solution was concentrated under reduced pressure, and the residue obtained was extracted with 20 ml of chloroform. The chloroform layer was washed with a 5% aqueous solution of potassium hydrogen sulfate, dried over anhydrous sodium sulfate and then concentrated under reduced pressure The residue was purified by preparative thin layer chromatography {developer: chloroform-ethanol (20:1)} to yield 33.5 mg of 3-n-undecyloxy-4-n-undecyloxymethylbenzoic acid as colorless needles. Melting point: 61–63° C. EIMS: m/z 476 (M+).

EXAMPLE 17:

Preparation of 4-hydroxymethyl-3-n-undecyloxybenzoic acid

Dimethylformamide (4.9 ml) and a 1.0 N aqueous solution of sodium hydroxide (0.49 ml) were successively mixed with 83.0 mg of methyl 4-hydroxymethyl-3-nundecyloxybenzoate to form a liquid suspension. The suspension was stirred at room temperature for 24 hours.

The resulting reaction solution which had become uniform was concentrated under reduced pressure, and the residue was extracted with 20 ml of chloroform. After washing the extract in chloroform with a 5% aqueous solution of potassium hydrogen sulfate, the extract solution was dried over anhydrous sodium sulfate and then concentrated to a small volume under reduced pressure The resultant thick solution was purified by preparative thin layer chromatography {developer: chloroform-ethanol (10:1)} to afford 32.2 mg of 4-hydroxymethyl-3-n-undecyloxybenzoic acid as a white solid. Melting point: 82–83° C. EIMS: m/z (M+)

EXAMPLE 18:

Preparation of n-octadecyl 3-n-octadecyloxy-4-n-octadecyloxymethylbenzoate

Anhydrous dimethylformamide (10 ml) was mixed with 100 mg of 3-hydroxy-4-hydroxymtthylbenzoic acid and 95.2 mg of 60% sodium hydride in oil. n-Octadecyl iodide (905 mg) was then added, and the resultant mixture was stirred at room temperature for 24 hours. n-Octadecyl iodide (300 mg) and chloroform (6.0ml) were added further, followed by stirring the resultant mixture at room temperature for 24 hours.

The resulting reaction solution was then added dropwise to 100 ml of a 5% aqueous solution of potassium hydrogen sulfate, followed by extraction with 100 ml of chloroform. The extract in chloroform was washed with water, dried over anhydrous sodium sulfate and then concentrated under reduced pressure. The residue was purified by chromatography on a silica gel column {developer: n-hexane-chloroform (2:1)}, to give 203 mg of n-octadecyl 3-n-octadecyloxy-4-n-octadecyloxymethylbenzoate as a white solid.

EXAMPLE 19:

Preparation of 3-n-octadecyloxy-4-n-octadecyloxymethylbenzoic acid

Tetrahydrofuran (30 ml), a 10% aqueous solution of sodium hydroxide (2.0 ml) and methanol (8.0 ml) were mixed with 195 mg of n-octadecyl 3-n-octadecyloxy-4-n-octadecyloxymethylbenzoate to form a solution. The solution was left over at room temperature for 24 hours.

The reaction solution obtained was concentrated under reduced pressure, followed by extraction with 100 ml of chloroform. After successively washing the extract in chloroform with a 5% aqueous solution of potassium hydrogen sulfate and water, the extract was dried over anhydrous sodium sulfate and then concentrated under reduced pressure. The residue was purified by preparative thin layer chromatography {developer: toluene-ethyl acetate (4:1)} to give 84.8 mg of 3-n-octadecyloxy-4-n-octadecyloxymethylbenzoic acid as a white solid. Melting point: 87–88° C. EIMS: m/z 672 (M+).

EXAMPLE 20:

Preparation of 0-isopropylidene-3-hydroxy-4-hydroxymethylbenzoic acid

Acetone (2.0 ml) was added to 100 mg of 3-hydroxy-4-hydroxymethylbenzoic acid to dissolve the latter compound. Thereafter, 15.0 mg of pyridinium p-toluenesulfonate and 68 μl of 2-methoxypropene were added. The resultant mixture was left over at room temperature for 24 hours.

The reaction solution obtained was added dropwise to 10 ml of a saturated aqueous solution of sodium hydrogen carbonate. The resulting mixture was concentrated under reduced pressure to remove acetone therefrom. The remaining aqueous phase was washed with chloroform, and then mixed with a 5% aqueous solution of potassium hydrogen sulfate to adjust the pH to 3–4. The resultant solution was extracted twice with 10 ml of chloroform, and the chloroform extract was dried over anhydrous sodium sulfate. The chloroform solution was concentrated under reduced pressure, and the residue was purified by preparative thin layer chromatography {developer: chloroform-methanol (10:1)} to give 74.3 mg of O-isopropylidene-3-hydroxy-4-hydroxymethylbenzoic acid as a white solid. Melting point: 153–156° C. EIMS: m/z 208 (M+).

Further, the preparation of some exemplary compounds of the benzoic acid derivative of the general formula (II) where n is zero, is illustrated with reference to the following Referential Examples 1–4.

Referential Example 1

Preparation of 3,4-di-n-hexyloxybenzoic acid

Anhydrous dimethylformamide (20 ml) was mixed with 200 mg of protocatechuic acid and 208 mg of 60% sodium hydride in oil, followed by addition of 912 μl of n-hexyl bromide. The resultant mixture was then stirred at room temperature for 24 hours. The reaction solution obtained was added dropwise to 200 ml of a 5% aqueous solution of potassium hydrogen sulfate, followed by extraction with 200 ml of chloroform. The chloroform extract was washed with water, dried over anhydrous sodium sulfate and then concentrated under reduced pressure.

A brown oil thus obtained was purified by chromatography on a silica gel column {developer: hexane-chloroform (3:2)} to give 441 mg of a colorless oil. Tetrahydrofuran (22 ml), a 10% aqueous solution of sodium hydroxide (4.4 ml) and methanol (11 ml) were successively added to the colorless oil, whereby the colorless oil was dissolved. The resultant solution was left over at room temperature for 48 hours. The solution was concentrated under reduced pressure and the residue obtained was extracted with 100 ml of chloroform. The chloroform solution was washed successively with a 5% aqueous solution of potassium hydrogen sulfate and water, and then dried over anhydrous sodium sulfate.

The chloroform solution was concentrated under reduced pressure, and the residue was purified by chromatography on a silica gel column {developer: chloroform-ethanol (30:1)} to yield 271 ml of the titled compound as colorless plate crystals. This compound is new. Melting point: 124–126° C. EIMS: m/z 322 (M+)

Referential Example 2

(a) Preparation of benzhydryl protocatechuate

Ethyl acetate (2.5 ml) was mixed with 50.0 mg of protocatechuic acid and 63.0 mg of diphenyldiazomethane to form a solution. The solution was left over at room temperature for 2 hours. Diphenyldiazomethane (25.8 mg) was added further and the resultant mixture was left over at room temperature for 2 hours. The pale reddish purple-colored reaction solution was concentrated under reduced pressure, and the colorless residue obtained was purified by chromatography on a silica gel column {developer: chloroform - chloroform-methanol (30:1)} to obtain 58.1 mg of the titled compound as a colorless syrup. EIMS: m/z 320 (M+).

(b) Preparation of 3,4-di-n-undecyloxybenzoic acid

Anhydrous diemthylformamide (4.9 ml) was mixed with 49.0 mg of the benzhydryl protocatechuate and 13.5 mg of 60% sodium hydride in oil, to form a mixture as a suspension. n-Undecyl iodide (77.8 µl) was then added, followed by stirring the resultant mixture at room temperature for 2 hours. The resulting reaction solution was added dropwise to 50 ml of a 5% aqueous solution of potassium hydrogen sulfate, followed by extraction with 50 ml of chloroform. The chloroform extract was dried over anhydrous sodium sulfate and then concentrated under reduced pressure to remove chloroform alone therefrom.

Trifluoroacetic acid (5.0 ml) was added to the remaining solution in dimethylformamide. The resultant mixture was left over at room temperature for 30 minutes. The solution was concentrated under reduced pressure and the residue was extracted with 50 ml of chloroform. The extract was washed with a 2.5% aqueous solution of potassium hydrogen sulfate, dried over anhydrous sodium sulfate, and then concentrated under reduced pressure. The residue was purified by preparative thin layer chromatography {developer: chloroform-methanol (10:1)} to obtain 48.5 mg of the titled compound as a colorless solid. This compound is new. Melting point: 98–101° C. EIMS: m/z 462 (M+).

Referential Example 3

Preparation of 3,4-di-n-octadecyloxybenzoic acid

Anhydrous dimethylformamide (5.1 ml) was mixed with 51.3 mg of benzhydryl protocatechuate and 14.0 mg of 60% sodium hydride in oil, to form a mixture as a suspension. n-Octadecyl iodide (134 mg) was then added to the suspension, followed by stirring the mixture at room temperature for 2 hours. The reaction solution obtained was added dropwise to 50 ml of a 2.5% aqueous solution of potassium hydrogen sulfate, followed by extraction with 50 ml of chloroform. The chloroform extract was dried over anhydrous sodium sulfate and then concentrated under reduced pressure to remove chloroform alone therefrom.

Trifluoroacetic acid (5.0 ml) was added to the remaining solution in dimethylformamide. Chloroform (5.0 ml) was added further, and the resultatt mixture was left over at room temperature for 10 minutes. The solution was concentrated under reduced pressure and the residue was extracted with 50 ml of chloroform. The extract was washed with a 2.5% aqueous solution of potassium hydrogen sulfate, dried over anhydrous sodium sulfate, and then concentrated under reduced pressure. The residue was purified by preparative thin layer chromatography {developer: chloroform-methanol (10:1)} to obtain 47.3 mg of the titled compound as a colorless solid This compound is new. Melting point: 94–117° C. EIMS: m/z 658 (M+)

Referential Example 4

Preparation of 3,4-di-n-valeryloxybenzoic acid

Anhydrous pyridine (2.0 ml) was added to 67.5 mg of benzhydryl protocatechuate to dissolve the latter compound, followed by addition of 55.9 mg of n-valeryl chloride. The resultant mixture was then left over at room temperature for 24 hours to effect the reaction. Water (17 µl) was added to the resulting reaction solution, followed by concentration under reduced pressure. The residue was extracted with 30 ml of chloroform. The extract was washed successively with a 5% aqueous solution of potassium hydrogen sulfate, a saturated aqueous solution of sodium hydrogen carbonate and water, and was then dried over anhydrous sodium sulfate.

The dried extract was concentrated under reduced pressure to obtain a yellowish oil. Trifluoroacetic acid (1.0 ml) was added to 92.8 mg of the yellowish oil to dissolve same. The resultant solution was left over at room temperature for 10 minutes and then was concentrated under reduced pressure, and the residue was twice subjected to azeotropic distillation with toluene. The residue was thereafter purified by preparative thin layer chromatography {developer: chloroform-methanol (8:1)} to obtain 24.8 mg of the titled compound as a colorless solid. This compound is new. Melting point: 97–103° C. EIMS: m/z 322 (M+).

We claim:

1. An anthracycline derivative having the general formula (I):

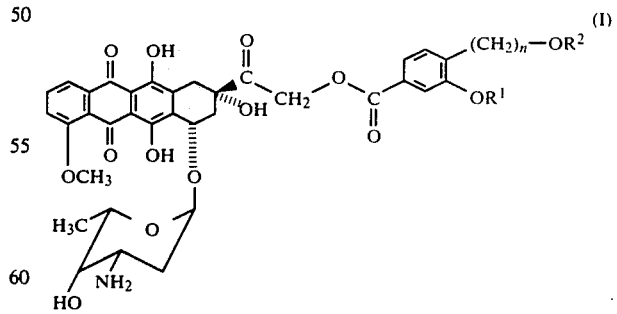

wherein $R^1$ and $R^2$ are the same or different and each denote a hydrogen atom or a straight or branched alkyl group of 1 to 18 carbon atoms, aralkyl group or an aryl group or an acyl group, or $R^1$ and $R^2$ taken together form a straight or branched alkylene group of 1 to 6 carbon atoms, an alkylidene group of 2 to 6 carbon atoms or an cycloalkylidene group of 3 to 6 carbon atoms, and n is an integer of 0 or 1, or an acid addition salt thereof.

2. An anthracycline derivative as claimed in claim 1 and having the formula (Ia):

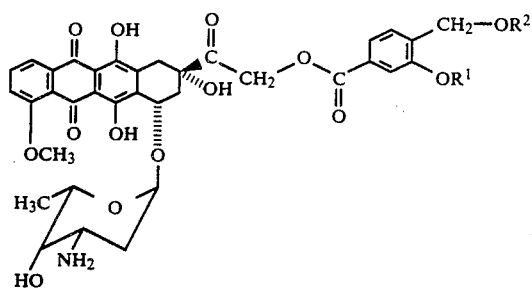

wherein $R^1$ and $R^2$ are the same or different and each denote a hydrogen atom or a straight or branched alkyl group of 1 to 18 carbon atoms, a aralkyl group or an aryl group, or $R^1$ and $R^2$ taken together form a straight or branched alkylene group or 1 to 6 carbon atoms, an alkylidene group of 2 to 6 carbon atoms or a cycloalkylidene group of 3 to 6 carbon atoms, or an acid addition salt thereof.

3. An anthracycline derivative as claimed in claim 1 and having the formula (Ib):

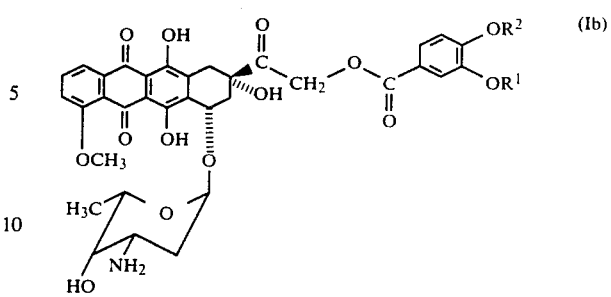

wherein $R^1$ and $R^2$ are the same and each denote a hydrogen atom or a straight or branched alkyl group of 1 to 18 carbon atom, a aralkyl group, an aryl group or an acyl group, or an acid addition salt thereof.

4. A compound of the general formula (I) as claimed in claim 1 or an acid addition salt thereof, where $R^1$ and $R^2$ are each a methyl group.

5. A compound of the general formula (I) as claimed in claim 1 or an acid addition salt thereof, where $R^1$ and $R^2$ are each a hexyl group.

6. A compound of the general formula (I) as claimed in claim 1 or an acid addition salt thereof, where $R^1$ and $R^2$ are each an undecyl group.

7. A compound of the general formula (I) as claimed in claim 1 or an acid addition salt thereof, where $R^1$ is an undecyl group and $R^2$ is a hydrogen atom.

8. A compound of the general formula (I) as claimed in claim 1 or an acid addition salt thereof, where $R^1$ and $R^2$ are each an octadecyl group.

9. A compound of the general formula (I) as claimed in claim 1 or an acid addition salt thereof, where $R^1$ and $R^2$ are each a hydrogen atom.

10. A compound of the general formula (I) as claimed in claim 1 or an acid addition salt thereof, where $R^1$ and $R^2$ taken together form an isopropylidne group $=C(CH_3)_2$.

11. A compound of the general formula (I) as claimed in claim 1 or an acid addition salt thereof, where an acyl group for $R^1$ or $R^2$ is an alkanoyl group of 2 to 6 carbon atoms.

12. A compound of the general formula (I) as claimed in claim 1 or an acid addition salt thereof, where $R^1$ and $R^2$ are each a valeryl group.

* * * * *